United States Patent
Tohma et al.

(10) Patent No.: US 6,861,565 B2
(45) Date of Patent: Mar. 1, 2005

(54) PROCESS FOR PRODUCING A FLUOROALKANOL

(75) Inventors: Toshihiko Tohma, Ichihara (JP); Akihiro Wada, Ichihara (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 10/383,688

(22) Filed: Mar. 10, 2003

(65) Prior Publication Data
US 2003/0158452 A1 Aug. 21, 2003

Related U.S. Application Data

(63) Continuation of application No. PCT/JP01/07711, filed on Sep. 5, 2001.

(30) Foreign Application Priority Data

Sep. 8, 2000 (JP) .......................................... 2000-273711

(51) Int. Cl.⁷ .......................... C07C 31/34; C07C 31/38; C07C 31/42; C07C 31/44
(52) U.S. Cl. ....................... 568/842; 570/138; 570/142; 570/175
(58) Field of Search ........................... 568/842; 570/138, 570/142, 175

(56) References Cited

U.S. PATENT DOCUMENTS 4,346,250 A * 8/1982 Satokawa et al. ........... 568/842

FOREIGN PATENT DOCUMENTS

| JP | 56-43225 | | 4/1981 |
| JP | 3-5434 | | 1/1991 |
| JP | 9-132542 | | 5/1997 |
| RU | 2150459 | * | 6/2000 |

OTHER PUBLICATIONS

U.S. Appl. No. 10/077,794, filed Feb. 20, 2002, Wada et al.
U.S. Appl. No. 10/383,688, filed Mar. 10, 2003, Tohma et al.
U.S. Appl. No. 10/028,827, filed Dec. 28, 2001, Wada et al.

* cited by examiner

*Primary Examiner*—Elvis O. Price
(74) *Attorney, Agent, or Firm*—Oblon, Spivak, McClelland, Maier & Neustadt, P.C.

(57) ABSTRACT

A process for producing a fluoroalkanol which can easily be industrially practiced with high selectivity, is provided.

$CHR^1R^2OH$, a radical initiator and $CF_2\!=\!CFR^f$ are continuously supplied and reacted at from 105 to 135° C., and $H\!-\!(R^f CFCF_2)_n\!-\!CR^1R^2\!-\!OH$ formed, is continuously discharged. Here, each of $R^1$ and $R^2$ is a hydrogen atom or a $C_{1-3}$ alkyl group, $R^f$ is a fluorine atom or a $C_{1-4}$ polyfluoroalkyl group, and n is an integer of from 1 to 4.

9 Claims, 1 Drawing Sheet

PROCESS FOR PRODUCING A FLUOROALKANOL

TECHNICAL FIELD

The present invention relates to a process for producing a fluoroalkanol.

BACKGROUND ART

A fluoroalkanol is useful as an intermediate for e.g. a water and oil repellent, a surfactant or a photographic color-developing material (e.g. JP-A-54-154707). Further, such a compound presents no solubility to a plastic substrate of e.g. polycarbonate and thus is useful as a solvent for an optical recording material, a dye, etc. (JP-A-4-8585, JP-A-5-258346, etc.).

Heretofore, a fluoroalkanol has been produced, for example, by a method of adding tetrafluoroethylene to methanol. As such a method, (1) a method wherein methanol, tetrafluoroethylene and a radical initiator are charged all at once and heated (U.S. Pat. No. 2,559,628), (2) a method wherein methanol, tetrafluoroethylene and a radical initiator are charged all at once and continuously reacted in a reaction column (U.S. Pat. No. 3,022,356), (3) a method wherein methanol and a radical initiator are charged all at once, and tetrafluoroethylene is continuously added and reacted (JP-A-54-154707), or (4) a method wherein tetrafluoropropanol and various telogens, are continuously reacted in the presence of a catalyst, at a temperature of not higher than 100° C. (JP-B-42-10782), has, for example, been known.

However, the method (1) has a problem that it is difficult to control the number of addition of tetrafluoroethylene, and even if it is attempted to obtain only a highly useful desired product having a number of addition of from 1 to 4, the molecular weight distribution of the product tends to be broad, and the yield tends to be low.

The method (2) has a problem that compounds having a number of addition of tetrafluoroethylene of 3 or more, are mainly formed, while a product having a number of addition of tetrafluoroethylene of 1 to 2 is small. The method (3) has a problem that it is necessary to add a solid acid scavenger, or it takes a long time for the reaction. Further, the method (4) has a problem that the concentration of the obtained telomer is as low as about 10%, and the average degree of polymerization tends to be extremely high at a level of 32, while the amount of products having a number of addition of from 1 to 4 tends to be extremely low.

DISCLOSURE OF THE INVENTION

It is an object of the present invention to solve the above problems and to provide a process for producing a fluoroalkanol, whereby mass production is possible with high yield and which is advantageous for industrial operation.

Namely, the present invention provides a process for producing a fluoroalkanol (formula 1), which comprises reacting a polyfluoroolefin (formula 2) and an alkanol (formula 3) in the presence of a radical initiator, wherein the polyfluoroolefin (formula 2), the alkanol (formula 3) and the radical initiator are continuously supplied into a reactor and reacted at from 105 to 135° C., and the fluoroalkanol (formula 1) formed, is continuously discharged:

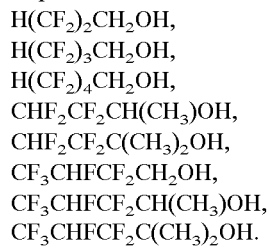

| | |
|---|---|
| H—$(R^fCFCF_2)_n$—$CR^1R^2$—OH | Formula 1 |
| $R^fCF=CF_2$ | Formula 2 |
| $CHR^1R^2$—OH | Formula 3 | provided that the symbols in the formulae have the following meanings:

$R^f$: a fluorine atom or a $C_{1-4}$ polyfluoroalkyl group;
$R^1$, $R^2$: each independently, a hydrogen atom or a $C_{1-3}$ alkyl group; and
n: an integer of from 1 to 4.

BEST MODE FOR CARRYING OUT THE INVENTION

Figure 1:
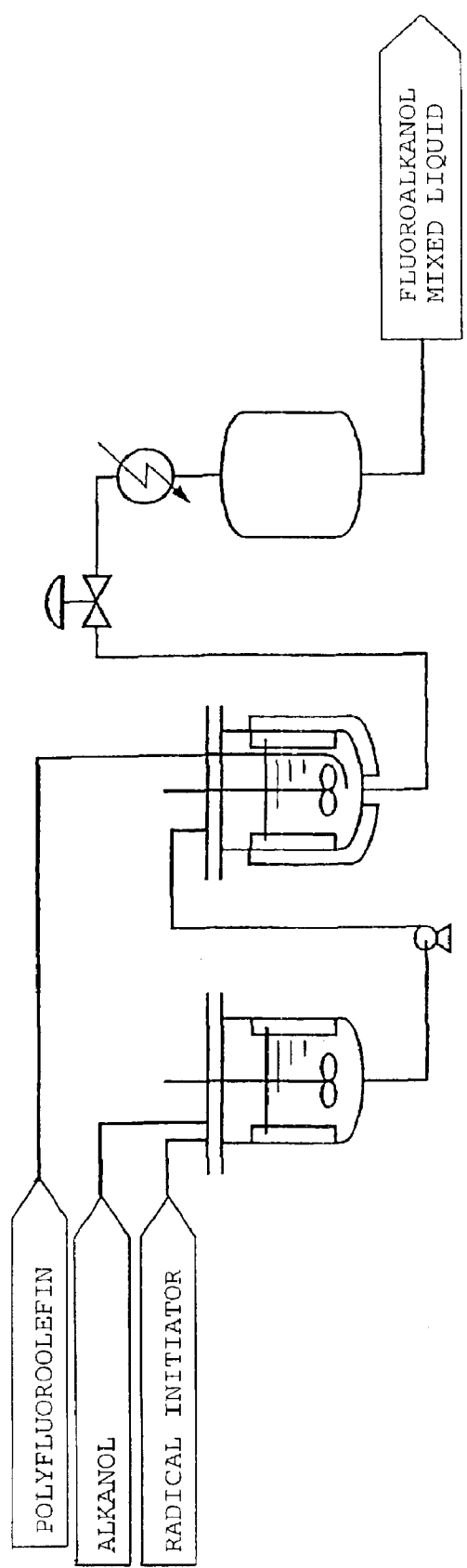
FIG. 1 is a flow chart showing one embodiment of the present invention.

In the formula (1), $R^f$ is a fluorine atom or a $C_{1-4}$ polyfluoroalkyl group. The polyfluoroalkyl group is a group having at least two hydrogen atoms in an alkyl group substituted by fluorine atoms. The polyfluoroalkyl group may be of a linear structure or a branched structure. $R^f$ is preferably a fluorine atom or a $C_{1-2}$ polyfluoroalkyl group, particularly preferably a fluorine atom or a trifluoromethyl group.

In the formula (1), each of $R^1$ and $R^2$ which are independent of each other, is a hydrogen atom or a $C_{1-3}$ alkyl group. The $C_{1-3}$ alkyl group may be a methyl group, an ethyl group, a n-propyl group or an isopropyl group.

In the formula (1), n is an integer of from 1 to 4, preferably 1 or 2.

The following compounds may be mentioned as specific examples of the fluoroalkanol (formula 1).

$H(CF_2)_2CH_2OH$,
$H(CF_2)_3CH_2OH$,
$H(CF_2)_4CH_2OH$,
$CHF_2CF_2CH(CH_3)OH$,
$CHF_2CF_2C(CH_3)_2OH$,
$CF_3CHFCF_2CH_2OH$,
$CF_3CHFCF_2CH(CH_3)OH$,
$CF_3CHFCF_2C(CH_3)_2OH$.

$R^f$ in the polyfluoroolefin (formula 2) has the same meaning as $R^f$ in the formula 1. The polyfluoroolefin (formula 2) is preferably a perfluoroolefin, and specifically, the following compounds may, for example, be mentioned:

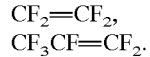

$CF_2=CF_2$,
$CF_3CF=CF_2$.

$R^1$ and $R^2$ in the alkanol (formula 3) have the same meanings as $R^1$ and $R^2$ in the formula 1. The following compounds may be mentioned as specific examples of the alkanol (formula 3):

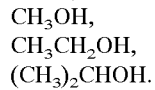

$CH_3OH$,
$CH_3CH_2OH$,
$(CH_3)_2CHOH$.

As the radical initiator to be used in the present invention, an organic free radical initiator may be mentioned. As such an organic free radical initiator, an organic peroxide or an azo compound is preferred, and particularly preferred is an organic peroxide such as an alkyl hydroperoxide, a dialkyl peroxide, a peroxyketal, a diacyl peroxide, a peroxycarboxylate, a peroxycarboxylic acid or a peroxycarbonate.

The following compounds may be mentioned as specific examples of the radical initiator.

1,1-bis(tert-butylperoxy)-3,3,5-trimethylcyclohexane, 1,1-bis(tert-butylperoxy)cyclohexane, tert-butylperoxyisopropyl carbonate, tert-butylperoxy isobutyrate, tert-butylperoxy pivalate, di-tert-butyl peroxide, and tert-butyl hydroperoxide.

Among radical initiators, a dialkyl peroxide which has a particularly high ability for forming radicals from the alkanol (formula 3), is preferred, and particularly preferred is di-tert-butyl peroxide.

The amount of the radical initiator to be supplied, is preferably from 0.0001 to 0.1 times by mol, particularly preferably from 0.001 to 0.05 times by mol, to the alkanol (formula 3). The amount of the polyfluoroolefin (formula 2) to be supplied, is preferably from 0.01 to 1.2 times by mol, particularly preferably from 0.05 to 0.5 times by mol, to the alkanol (formula 3).

The present invention provides a process for producing a fluoroalkanol (formula 1), wherein the polyfluoroolefin (formula 2), the alkanol (formula 3) and the radical initiator, are continuously supplied into a reactor and reacted at from 105 to 135° C., and the fluoroalkanol (formula 1) is continuously discharged. It is preferably carried out in the following manner.

Namely, the polyfluoroolefin (formula 2) is preferably supplied into a reactor having the alkanol (formula 3) charged, so that the pressure in the reactor would be preferably from 0.2 to 1.5 MPa (gauge pressure, the same applies hereinafter), particularly preferably, from 0.5 to 1.0 MPa.

On the other hand, the alkanol (formula 3) and the radical initiator are preferably continuously supplied into the reactor in the form of their mixed solution. And, during the reaction, the formed fluoroalkanol (formula 1) is preferably discharged from the reactor, so that the liquid level in the reactor would be constant.

Now, the process for producing a fluoroalkanol of the present invention will be described in further detail with reference to the drawing.

FIG. 1 is a flow chart showing one embodiment of the present invention.

A reaction tank is used as a reactor, and the reaction tank is provided with a line to supply a mixed solution of the alkanol (formula 3) and the radical initiator continuously by a pump from a blending tank to the reaction tank, and a line to supply the polyfluoroolefin (formula 2). Further, the reaction tank is connected to a reaction liquid storage tank to withdraw a liquid (hereinafter referred to as a reaction liquid) containing the fluoroalkanol (formula 1) formed by the reaction in the reaction tank and to store the reaction liquid.

Firstly, the alkanol (formula 3) and the radical initiator are mixed in the blending tank equipped with a stirring device to prepare their mixed solution. On the other hand, the alkanol (formula 3) is charged to the reaction tank equipped with a stirring device, and the reactor is heated to from 105 to 135° C. Then, while continuously supplying the polyfluoroolefin (formula 2) to the reaction tank, the previously prepared mixed solution of the alkanol (formula 3) and the radical initiator, is continuously supplied by a pump to the reaction tank. At the same time, the reaction liquid is withdrawn to the reaction liquid storage tank, so that the liquid level in the reaction tank would be constant. On the other hand, the polyfluoroolefin (formula 2) is also continuously supplied. From the reaction liquid stored in the reaction liquid storage tank, the fluoroalkanol (formula 1) can be obtained via a purification method such as cooling or distillation.

The reaction of the alkanol (formula 3) and the polyfluoroolefin (formula 2) is so-called a telomerization reaction. The telomerization reaction is a chain reaction wherein the radical initiator is decomposed to form a radical, and the radical will withdraw a hydrogen atom on the carbon on which the hydroxyl group of the alkanol (formula 3) is bonded, to form an alkanol radical, and the polyfluoroolefin (formula 2) is added thereto. And, the reaction in the present invention is a reaction whereby the number of addition of the polyfluoroolefin (formula 2) can be controlled in such a telomerization reaction as a chain reaction, whereby the desired fluoroalkanol (formula 1) wherein n is from 1 to 4, can be obtained in high yield.

Among the reaction conditions, firstly, the reaction temperature is required to be from 105 to 135° C. For example, in a case where it is desired to obtain an object wherein n is 1 or 2, or in a case where di-tert-butyl peroxide (the temperature at which half life is 10 hours: 125° C.) is used as a radical initiator, the temperature is preferably within a range of from 120 to 130° C. as an industrially advantageous condition. The reaction time is preferably at least 3 hours, particularly preferably at least 5 hours. Further, the upper limit of the reaction time is not particularly limited. The average retention time calculated by dividing the amount of the reaction liquid in the reactor by the supply rate of the starting material, is preferably from 2 to 100 hours from the viewpoint of the conversion, and it is particularly preferably from 5 to 20 hours, as an industrially advantageous condition. The reaction pressure is preferably from 0.2 to 1.5 MPa, particularly preferably from 0.5 to 1.0 MPa from the viewpoint of the conversion.

Further, with respect to the supply of the radical initiator and the alkanol (formula 3), an irregular supply method may be adopted at the initial stage of the reaction in order to initiate the reaction under a stabilized condition, but after the reaction is stabilized, it is preferred to supply them at a constant rate during the reaction time. Further, also with respect to the polyfluoroolefin (formula 2), it is preferred to supply the necessary total amount at a constant rate during the reaction time.

Furthermore, according to the process of the present invention, the amount of addition can easily be controlled by adjusting the amount of the polyfluoroolefin (formula 2) to be supplied, whereby it is possible to obtain the fluoroalkanol (formula 1) with high selectivity and high productivity. The obtained fluoroalkanol (formula 1) is subjected to usual separation purification to obtain one having a high purity. Further, in the method of the present invention, the product, etc. will be continuously discharged, whereby accumulation of an acid content will be suppressed, and it is advantageous that the reaction can be carried out in the absence of an acid scavenger (i.e. without an acid scavenger).

The fluoroalkanol (formula 1) produced by the process of the present invention, is useful as a starting material or a solvent for a water and oil repellent, a surfactant, a photographic color-developing material, etc.

EXAMPLES

Now, the present invention will be described in detail with reference to Examples, but the present invention is by no means thereby restricted. In the following, liter will be represented by "1". Further, % determined by gas chromatography is based on mass.

Example 1

Production of 2,2,3,3-tetrafluoro-1-propanol

The reaction was carried out in accordance with the flow chart as shown in FIG. 1. Namely, a 1 m³ hastelloy C reaction tank equipped with a stirring device, was used as the reactor, and 341 kg (432 l) of methanol was charged thereto. Then, the internal temperature was raised to 125° C. While maintaining this temperature and supplying tetrafluoroethylene to the reaction tank so that the pressure would be 0.9 MPa, at the initial stage of the reaction, a solution having 5.5 kg of di-tert-butyl peroxide and 44 kg of methanol mixed in the blending tank, was continuously supplied to the reaction tank by means of a metering pump at a rate of 25 l/hr for 0.5 hour, and thereafter, continuously supplied at a rate of 4.2 l/hr for few hours, to carry out the reaction.

Then, while continuously supplying tetrafluoroethylene so that the pressure in the reaction tank would be 0.9 MPa, a solution having 12 kg of di-tert-butyl peroxide and 1,315 kg of methanol mixed in the blending tank, was continuously supplied to the reaction tank by means of a metering pump at a rate of 56 l/hr, and from the bottom of the reaction tank, the reaction liquid was continuously discharged to the reaction storage tank, so that the liquid level would be constant. Such continuous supply and continuous discharge of the reaction liquid, were carried out for 110 hours. After the 110 hours, supply of a methanol solution of di-tert-butyl peroxide, was terminated, and then tetrafluoroethylene was supplied to the reaction tank so that the pressure would be 0.9 MPa. After maintaining the temperature at 125° C. for 3 hours, it was cooled to 40° C. As a result, using a total of 4.9 t of methanol and a total of 1.9 t of tetrafluoroethylene, as a reaction liquid, 6.7 t of a mixed liquid comprising 2,2,3,3-tetrafluoro-1-propanol and methanol, was obtained.

The mixed liquid was analyzed by gas chromatography, whereby it contained 66% of methanol, 28% of 2,2,3,3-tetrafluoro-1-propanol, and 4% of 2,2,3,3,4,4,5,5-octafluoro-1-pentanol. Further, the conversion of methanol was 15%, and selectivity for 2,2,3,3-tetrafluoro-1-propanol was 93%, and the selectivity for 2,2,3,3,4,4,5,5-octafluoro-1-pentanol was 7%. This mixture was purified by distillation to obtain 2,2,3,3-tetrafluoro-1-propanol having a purity of at least 99%.

Example 2

Production of 2,2,3,4,4,4-hexafluoro-1-butanol

A reaction was carried out in accordance with the flow chart as shown in FIG. 1. Namely, a 0.5 m³ hastelloy C reaction tank equipped with a stirring device, was used as the reactor, and 170 kg (212 l) of methanol was charged thereto. Then, the internal temperature was raised to 130° C. A solution having 2.8 kg of di-tert-butyl peroxide and 22 kg of methanol mixed in the blending tank, was continuously supplied to the reaction tank by means of a metering pump at an initial stage of the reaction at a rate of 25 l/hr for 0.25 hour, and thereafter, continuously supplied at a rate of 4.2 l/hr for 4 hours, to carry out the reaction. At the same time, 20 kg of hexafluoropropene was continuously supplied to the reaction tank by means of a metering pump at a rate of 3 l/hr. Then, a solution having 12 kg of di-tert-butyl peroxide and 1,315 kg of methanol mixed in the blending tank, was continuously supplied to the reaction tank by means of a metering pump at a rate of 28 l/hr, and at the same time, hexafluoropropene was continuously supplied to the reaction tank by means of a metering pump at a rate of 3 l/hr. During this period, from the bottom of the reaction tank, the reaction liquid was continuously discharged to the reaction storage tank, so that the liquid level would be constant. Such continuous supply of the starting materials and the continuous discharging of the content liquid, were carried out for 40 hours. Upon expiration of 40 hours, supply of the methanol solution of di-tert-butyl peroxide, was terminated, and then the temperature was maintained at 125° C. for one hour and then cooled to 40° C. As a result, as a reaction liquid, 1.2 t of a mixed liquid comprising of 2,2,3,4,4,4-hexafluoro-1-butanol and methanol, was obtained.

This mixed liquid was analyzed by gas chromatography, whereby it contained 73% of methanol and 19% of 2,2,3,4,4,4-hexafluoro-1-butanol. Further, the conversion of methanol was 8%, and selectivity for 2,2,3,4,4,4-hexafluoro-1-butanol was 88%. This mixture was purified by distillation to obtain 2,2,3,4,4,4-hexafluoro-1-butanol having a purity of at least 99%.

INDUSTRIAL APPLICABILITY

According to the present invention, a fluoroalkanol (formula 1) can be produced with high selectivity. Further, the process of the present invention is a continuous process wherein the starting materials are continuously supplied, and the product is continuously discharged, and it is a process which is extremely advantageous for industrial operation, since in that process, it is unnecessary to employ any special reaction conditions or reaction operation.

The entire disclosure of Japanese Patent Application No. 2000-273711 filed on Sep. 8, 2000 including specification, claims, drawings and summary is incorporated herein by reference in its entirety.

What is claimed is:

1. A continuous process for producing a fluoroalkanol of the following formula 1, which comprises reacting a polyfluoroolefin of the following formula 2 and an alkanol of the following formula 3 in the presence of a radical initiator, wherein the polyfluoroolefin of the following formula 2, the alkanol of the following formula 3 and the radical initiator are continuously supplied into a reactor and reacted at from 105 to 135° C., and the fluoroalkanol of the following formula 1 formed, is continuously discharged:

| | |
|---|---|
| H—(R$^f$CFCF$_2$)$_n$—CR$^1$R$^2$—OH | Formula 1 |
| R$^f$CF=CF$_2$ | Formula 2 |
| CHR$^1$R$^2$—OH | Formula 3 | provided that the symbols in the formulae have the following meanings:

R$^f$: a fluorine atom or a C$_{1-4}$ polyfluoroalkyl group;

R$^1$, R$^2$: each independently, a hydrogen atom or a C$_{1-3}$ alkyl group; and n: an integer of from 1 to 4.

2. The process for producing a fluoroalkanol according to claim 1, wherein n is 1 or 2.

3. The process for producing a fluoroalkanol according to claim 1, wherein the radical initiator is an organic peroxide.

4. The process for producing a fluoroalkanol according to claim 1, wherein the radical initiator is a dialkyl peroxide.

5. The process for producing a fluoroalkanol according to claim 1, wherein the fluoroalkanol of the formula 1 is 2,2,3,3-tetrafluoro-1-propanol, 2,2,3,3,4,4,5,5-octafluoro-1-pentanol or 2,2,3,4,4,4-hexafluoro-1-butanol.

6. The process for producing a fluoroalkanol according to claim 1, wherein the polyfluoroolefin of the formula 2 is a perfluoroolefin.

7. The process for producing a fluoroalkanol according to claim 1, wherein the reaction is carried out in the absence of an acid scavenger.

8. The process for producing a fluoroalkanol according to claim 1, wherein the polyfluoroolefin of the formula 2 is supplied so that the pressure in the reactor would be from 0.2 to 1.5 MPa (gauge pressure).

9. The process for producing a fluoroalkanol according to claim 1, wherein the formed fluoroalkanol of the formula 1 is discharged from the reactor so that the liquid level in the reactor would be constant.

* * * * *